(12) United States Patent
Leonard

(10) Patent No.: US 6,258,106 B1
(45) Date of Patent: Jul. 10, 2001

(54) SURGICAL KNOT PUSHER AND METHOD OF USE

(75) Inventor: Robert F. Leonard, Suwanee, GA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/397,907

(22) Filed: Sep. 17, 1999

Related U.S. Application Data

(60) Provisional application No. 60/100,969, filed on Sep. 18, 1998.

(51) Int. Cl.$^7$ .................................................. A61B 17/04
(52) U.S. Cl. ........................ 606/148; 606/144; 606/145
(58) Field of Search .................................. 606/139, 144, 606/145, 148

(56) References Cited

U.S. PATENT DOCUMENTS

| | | | | |
|---|---|---|---|---|
| 3,877,434 | * | 4/1975 | Ferguson et al. | 606/158 |
| 4,641,652 | * | 2/1987 | Hutterer et al. | 606/144 |
| 5,176,691 | * | 1/1993 | Pierce | 606/148 |
| 5,192,287 | * | 3/1993 | Fournier et al. | 606/139 |
| 5,217,471 | * | 6/1993 | Buhkart | 606/148 |
| 5,234,444 | * | 8/1993 | Christoudias | 606/148 |
| 5,281,236 | * | 1/1994 | Bagnato et al. | 606/139 |
| 5,364,410 | * | 11/1994 | Failla et al. | 606/148 |
| 5,454,821 | * | 10/1995 | Harm et al. | 606/148 |
| 5,643,292 | * | 7/1997 | Hart | 606/144 |
| 5,653,716 | * | 8/1997 | Malo et al. | 606/139 |

* cited by examiner

*Primary Examiner*—Gary Jackson
(74) *Attorney, Agent, or Firm*—Richard D. Allison; Thomas J. DesRosier

(57) ABSTRACT

A surgical knot pusher and method for use thereof to facilitate the tying of surgical sutures at remote sites within the body during endoscopic surgery and other minimally invasive surgical procedures, the knot pusher having a tubular, elongated housing having a passage defining a rod axis therethrough, a suture receiving tip forming a J-shaped hook defining a gap, a drive rod slidably disposed within the passage of the housing and extending substantially co-axial to the rod axis of the housing, wherein the drive rod is connected to the tip so that said tip is selectively operable between an open position, wherein axial movement of the drive rod relative to the housing causes a portion of the tip to extend beyond the distal end of the housing so that a length of suture may be inserted therein the gap of the hook of the tip, and a closed position, wherein axial movement of the drive rod relative to the housing causes the tip to be received within the passage of the housing proximate the distal end of the housing so that an eyelet having an aperture for releasably capturing the first length of the suture is formed, and a knot pushing surface formed from the exterior surface of the tip.

22 Claims, 4 Drawing Sheets

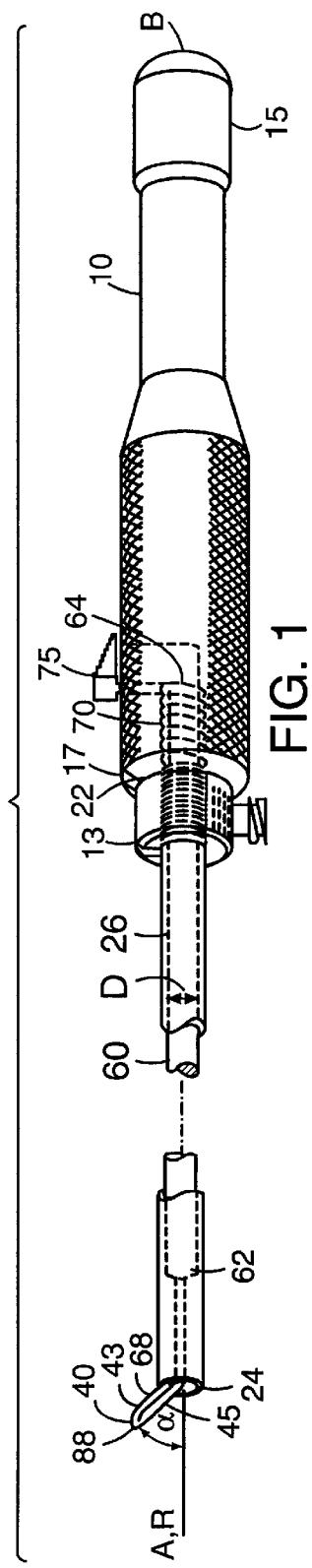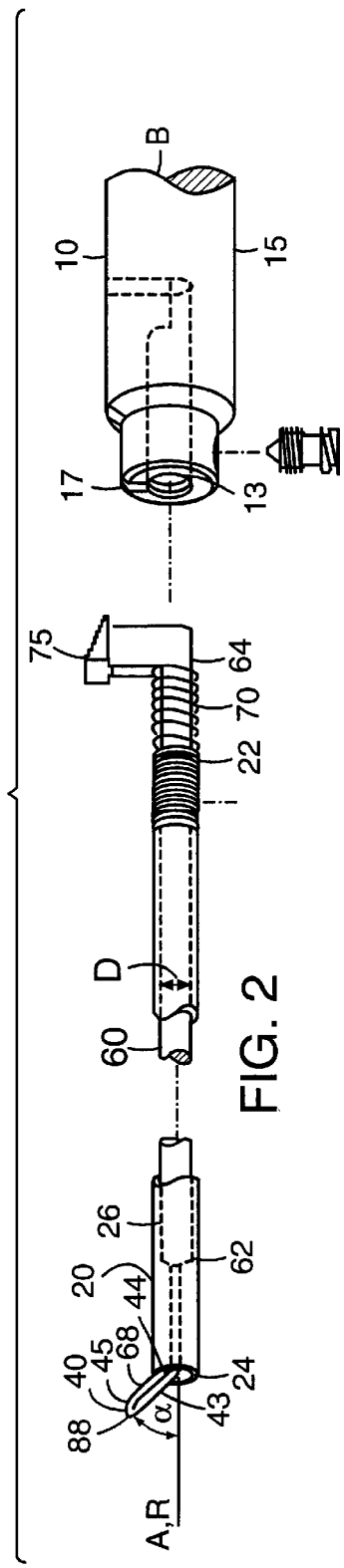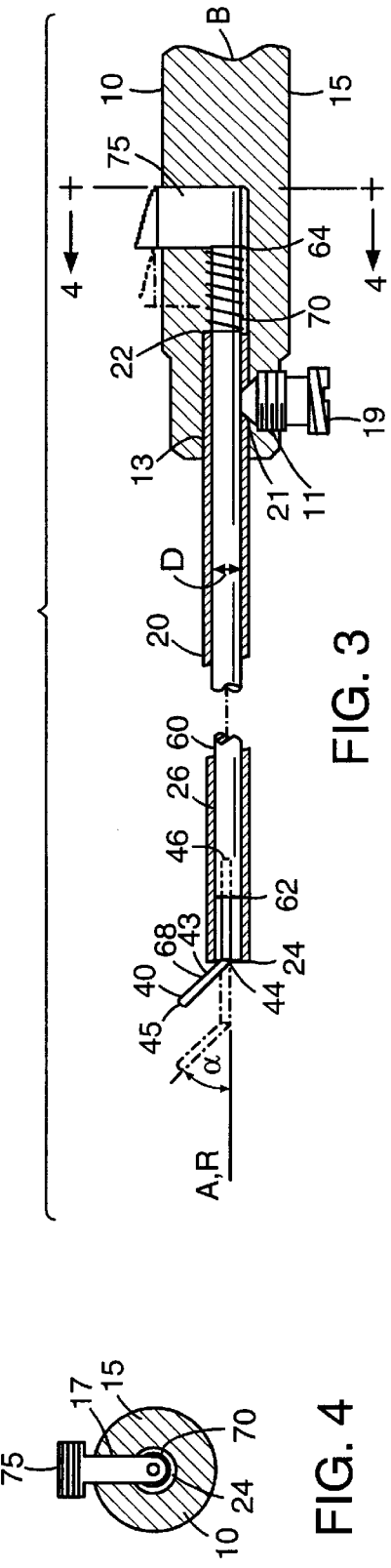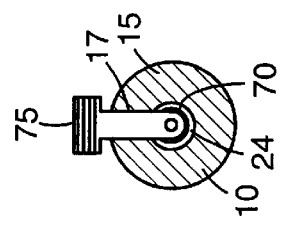

SURGICAL KNOT PUSHER AND METHOD OF USE

This application claims the benefit, pursuant to 35 U.S.C. § 120, of Applicant's provisional U.S. patent application Ser. No. 60/100,969, filed Sep. 18, 1998, entitled "Surgical Knot Pusher and Method of Use."

BACKGROUND OF THE INVENTION

1. Field of the Invention

The present invention relates to a device to facilitate the tying of surgical sutures at remote sites within the body during endoscopic surgery and other minimally invasive surgical procedures. A method for tying surgical knots in a suture at intracorporeal positions during minimally invasive surgery is also presented.

2. Background Art

Minimally invasive surgical techniques have emerged as an important trend within the field of surgery. Minimally invasive surgery differs from standard open surgery in that surgical procedures are performed through small incisions in the body under the guidance of endoscopy, fluoroscopy, ultrasound or other remote imaging techniques. Minimally invasive surgical techniques reduce the morbidity of surgical procedures, accelerate patient recovery and, in many cases, also reduce the overall cost of surgery, especially by shortening the recovery period during which patients must stay in the hospital.

Due to such benefits, many established surgical procedures, such as arthoscopic knee surgery and gall bladder removal, have been converted from open surgical techniques to minimally invasive surgical techniques. Minimally invasive surgery includes laparoscopic, endoscopic and orthoscopic surgeries. In performing laparoscopic surgery, for example, procedures are performed in the abdominal cavity by making a small incision through several layers of tissue, which may include the outer layer of skin called the epidermis, a layer of fat beneath the epidermis, a layer of abdominal muscle tissue beneath the fat layer and the lining of the abdominal cavity called the peritoneum. A trocar is inserted through the incision and medical instruments are introduced into the abdominal cavity therethrough. The surgeon performs procedures inside the cavity by manipulating the medical instruments from outside the patient while viewing the manipulations using a closed circuit monitor connected to an imaging device called a laparoscope that is inserted into the cavity. By using such equipment and procedures, laparoscopic surgery generally results in less trauma to the patient and, consequently, a more rapid recovery than with conventional open surgery. Similar advantages apply to other forms of minimally invasive surgery.

One of the great challenges facing minimally invasive surgery is the advancement of minimally invasive surgical techniques into the area of cardiac surgery. Certain cardiac surgery procedures that previously were only possible through open chest surgery have already been converted to minimally invasive surgical techniques. For example, catheter techniques have been developed for occlusion of patent material septal defects and for valvuloplasty of stenotic aortic or mitral valves. Instruments and techniques have also been developed for endoscopic approaches to the heart, allowing more complex cardiac surgical procedures, for example, the replacement of a stenotic or insufficient mitral valve, to be performed through minimally invasive surgical techniques.

One of the important challenges in minimally invasive surgical techniques is that of placing sutures in the tissue at the operating site and applying properly tied suture knots through the narrow access of an endoscopic cannula or other equally restrictive access passage. Two different approaches are commonly used in tying sutures in endoscopic surgery. These can be classified generally as intracorporeal knot tying techniques, for tying sutures at the surgical site within the body, and extracorporeal knot tying techniques, which allow knots to be tied in the sutures outside of the body, then transferred to the surgical site using a knot pusher.

Intracorporeal knot tying can be performed using endoscopic graspers or forceps to manipulate the sutures in a technique similar to instrumented knot tying in conventional surgery. Alternatively, specialized intracorporeal knot tiers can be used.

Various intracorporeal knot tiers are shown in U.S. Pat. No. 5,234,443 to Phan et al., U.S. Pat. No. 4,641,652 to Hutterer et al. and U.S. Pat. No. 5,281,236 to Bagnato et al. Tying sutures using a grasper or an intracorporeal knot tier is difficult and tedious compared with standard bimanual methods of surgical knot tying. Using intracorporeal knot tiers usually requires specialized training in operating the instrument and, even in the hands of the most skilled operators, usually requires more time than standard knot tying techniques. In procedures where few knots have to be tied, where access to the surgical site is difficult, or where the length of the procedure is not critical, intracorporeal knot is the likely method of choice.

However, for the surgical replacement of a diseased mitral valve using closed chest surgical procedures, the complexity and time consumption of using intracorporeal knot tying techniques can endanger the patient since the rate of post-surgical complications in cardiac procedures rises in proportion to the length of time that the patient must spend on cardiopulmonary bypass. The time spent using intracorporeal knot techniques in a surgical procedure, such as mitral valve replacement, that can involve tying a multitude of individual multiple-throw suture knots, with up to four (4) or more throws per suture, unnecessarily endangers the patient. Due to the proportional increase in patient risk, it is important to keep the duration of the procedure as short as possible and avoid any unnecessary delays.

Therefore, in time sensitive procedures, it is best to take advantage of an experienced surgeon's practiced and well honed bimanual surgical knot tying skill, rather than to require the surgeon to use complex intracorporeal knot tying techniques. Some knot pushers are designed specifically to take advantage of this prior skill by allowing the surgeon to form the suture knots extracorporeally, then using the knot pusher to transfer the knots to the surgical site and tighten them in place. A well designed knot pusher allows the surgeon to use a knot tying technique that closely mimics the standard bimanual knot tying technique and does not add undue complication to the procedure.

A common type of surgical knot pusher is made with a C-shaped loop on the distal end of an elongated shaft, as exemplified in U.S. Pat. No. 3,871,379 to Clarke. The opening of the C faces distally from the shaft, and the opening is sized to pass the desired size of suture. These devices are used by first passing the suture through the tissue to be tied and bringing both ends of the suture out through the surgical entry point so that a knot can be tied extracorporeally. The C-shaped loop is then placed over the knot and is used to slide the knot down the suture to the surgical site. The knot may then be tightened by pulling on the suture ends. This type of knot pusher has several disadvantages. The knot pusher must be reloaded onto the suture thread each time another throw is added to the suture knot. This adds time and complexity to the tying technique. In many cases, the orientation of the C-shaped loop on the knot pusher prevents the knot from being pushed directly up to the tissue that is to be sutured. This can leave a bit of slack in the suture that would be a severe problem in valve replacement surgery because it could cause the replacement valve to loosen and potentially displace from its proper position in the heart or could lead to perivalvar leaks. The open gap of the C-shaped loop can accidentally drop the suture while pushing the knot down if it is not carefully handled. This can be very frustrating to the surgeon because the knot pusher will have to be rethreaded, which is much more difficult once the knot is halfway down the suture and within the body cavity. Also, the knot pusher has no means to insure that the knot remains centered on the knot pusher. The surgeon must carefully maintain equal tension on both ends of the suture or the knot will slide sideways out of the C-shaped loop. While this type of knot pusher works well with monofilament sutures, it has been found to be ineffective and difficult to use for braided sutures, which are the type often preferred for valve replacement surgery. This is due to the fact that the narrow knot pushing edge within the C-shaped loop places too much pressure against the knot, which tends to make the knot lock up rather than slide along the suture.

Another type of knot pusher has a pair of opposing grooves on the head of the knot pusher with a flat surface between them. Examples of this type of knot pusher can be seen in U.S. Pat. No. 5,234,444 to Christoudias and U.S. Pat. No. 5,217,471 to Burkhart. The flat surface between the grooves allows the device to push directly against the tissue that is being sutured and it separates the two ends of the suture so that the tension to tighten the knot acts parallel to the tissue surface, which more effectively tightens the knot than pulling the sutures perpendicular to the tissue surface. However, these knot pushers have the disadvantages that they must be reloaded onto the suture every time another throw is added to the knot and they are even more prone to dropping knots than the devices previously described.

A number of surgical knot pushers have been designed to overcome the problem of dropping the knot while transporting it to the surgical site. In general, this type of knot pusher has a pair of eyelets on opposite sides of the head of the device. Examples of this type of knot pusher can be seen in U.S. Pat. No. 5,176,691 to Pierce and U.S. Pat. No. 5,192,287 to Fournier. The two eyelets are very effective at avoiding dropping the knot and at keeping the knot properly centered in front of the device. The disadvantage of having two eyelets is that it makes it more difficult to thread the device onto the ends of the sutures. In addition, each time another throw is added to the knot, at least one end of the suture must be unthreaded from the eyelet end then rethreaded after the knot is made. This adds undue time and complexity to the knot tying procedure.

Another detail of construction that is significant in mitral valve replacement surgery is that, when the replacement valve used is a mechanical valve as opposed to a bioprosthesis, the knot pusher must be made so that no metal parts can possibly come in contact with the mechanical replacement valve. This is because mechanical heart valves are made with highly polished surfaces that may also be coated with a hemocompatible coating such as pyrolytic carbon to reduce hemolysis and platelet attachment. Any disturbance in the surface of the valve or the coating could become a locus for increased hemolysis, thrombogenisis or platelet attachment and thrombosis. This could lead to possibly fatal post-surgical complications. Thus, at least the leading edge of the knot pusher should be made of plastic or another material that will not damage the surface of the replacement valve if there is accidental contact between them during installation. Many of the prior art knot pushing devices are impractical for construction out of plastic because of their complex geometries or a need for high strength in the moving parts. Therefore, they would not be suitable for use in valve replacement surgery.

SUMMARY OF THE INVENTION

In keeping with the foregoing discussion, a general objective of the present invention is to provide a surgical knot pusher suitable for use in endoscopic surgery and other minimally invasive surgical techniques that overcomes the disadvantages of the prior art.

The surgical knot pusher of the present invention facilitates a knot tying technique which closely mimics the bimanual suture tying technique used in open surgery. The knot pusher also allows for the efficient, non-time consuming, capture of the ends of the suture. The suture does not need to be recaptured for every additional throw of a surgical knot so that multiple-throw surgical knots can be formed quickly and easily. The knot pusher is highly resistant to dropping a knot while transporting it to the surgical site and it does not require being completely withdrawn in order to pick up a knot in the unlikely event that one slips off of the knot pusher during use. Further, the knot pusher allows the knot to be pushed directly against the tissue or material being sutured so that there is no slack left in the suture that could cause complications.

The knot pusher of the present invention is well adapted for forming symmetrical knots such as surgeons' knots, square knots and reef knots, which are preferred for mitral valve replacement surgery. This requires that the paths for the two ends of the suture material through the knot pusher should be symmetrical. For the proper tightening of these preferred types of knots, it is also required that tension applied to the ends of the suture material should be translated to the knot as a tension that is parallel to the surface of the tissue being sutured. The knot pusher of the present invention does not cause an undue amount of pressure to be placed directly on the knot that might otherwise cause the knot to lock up and jam the knot pusher.

In order that the knot pusher be usable with mechanical heart valves, as well as bioprosthetic valves, the design of the knot pusher is well suited for construction out of plastic or other materials compatible with the fragile hemocompatible coatings that are used on mechanical heart valves.

In accordance with these objectives, a preferred embodiment of the surgical knot pushing instrument has an elongated drive rod extending from a rear end to a front end. A suture receiving tip, having a J-shaped hook structure with a gap, is connected to the front end of the drive rod. The drive rod is slidably disposed within a tubular, elongated housing. When the drive rod is translated axially along the rod axis of the housing, the gap of the tip is selectively opened and closed. In the open position, the drive rod is translated axially so that the front end of the connected tip extends beyond the distal end of the housing which presents the gap of the tip for receipt of a first length of a suture. In the closed position, the drive rod is translated axially, in the opposite direction, so that both the front and back ends of the connected tip are disposed within the passage of the housing so that an eyelet having an aperture is formed for releasably capturing the first length of the suture.

The knot pushing instrument also has a knot pushing surface formed from the exterior surface of the tip. This knot pushing surface is formed from the curved portion of the tip as it bends to form the J-shaped hook. This curved portion defines an arc having a convex curvature and, in combination with the preferred circular cross section of the tip, forms a smooth continuous surface which helps prevent binding of the knot as it is pushed onto the surgical site.

The knot pushing instrument also has a push button connected to the rear end of the drive rod for applying force to the rod to axially translate the rod and the connected tip into the operatively open position for receipt of the first length of suture. Furthermore, the knot pushing instrument also has a spring disposed at the rear end of the rod to aid in applying force on the rod to bias the rod axially so that the tip is brought into the operatively closed position upon the release of the push button.

The surgical knot pusher of the present invention provides one of the essential instruments for facilitating minimally invasive surgery. In the typical minimally invasive surgery, the sutures are placed through the injured tissue and the free ends of the sutures extend into a manipulation area. At this point, the knot pusher is used to tie the sutures to secure the injured tissues. The two ends of a suture are located and one end of the suture is grasped by the hook on the knot pusher, when the knot pusher is in an operatively open position such that the front end of the tip is disposed beyond the distal end of the housing, and is captured within the aperture of the eyelet of the tip of the instrument when the drive rod is translated axially to an operatively closed position. In the closed position, the front and back the ends of the tip are disposed within the passage of the housing, which forms the eyelet of the tip for receipt of the captured end of the suture. The second end of the suture is thrown around the first end of the suture to form an overhand knot and the knot pusher is pushed along the captured suture end until meeting the knot. The knot pusher is then used to advance the knot along the respective lengths of the suture until the knot is tight against the surgical site. The knot pusher is withdrawn until the head of the device is outside of the body or within the manipulation area, and a second overhand knot is thrown in the opposite sense to the first knot. The second knot is advanced, using the same method illustrated above, until it is against the first knot so that a square knot is formed. A series of four or more throws may be made in the suture as desired by the surgeon and the ends of the suture are cut off. Thus, the device and method of the present invention provides a quick and efficient method for forming secure knots in sutures during minimally invasive procedures and avoids the time delays inherent in multiple rethreading required in prior art eyelet knot pushers.

Accordingly, it is a principal object of the present invention to provide a novel and improved medical instrument and method for tying knots in sutures, particularly for use in minimally invasive surgery.

It is another object of the present invention to provide a knot tying instrument and method for its use that, when used in minimally invasive surgery, allow knots to be tied while minimizing trauma to surrounding tissue.

It is a further object of the present invention to provide a knot tying instrument and method for its use that minimizes the manipulations necessary to tie knots during minimally invasive surgery.

It is yet another object of the present invention to provide a knot tying instrument and method that are easy and efficient to use in tying knots in sutures.

It is yet a further object of the present invention to provide a knot tying instrument and method that facilitate the tying of various knots, including square knots.

It is another object of the present invention to provide a knot tying instrument that is lightweight.

It is a further object of the present invention to provide a knot tying instrument that is simple in design and easy and inexpensive to manufacture.

The foregoing and other objects and advantages of the invention will no doubt occur to those skilled in the art upon reading and understanding the following detailed description along with the accompanying drawings.

BRIEF DESCRIPTION OF THE FIGURES OF THE DRAWINGS

Embodiments of the invention are described by way of example with reference to the accompanying drawings, in which:

FIG. 1 is a perspective side view of a knot pusher instrument according to the present invention;

FIG. 2 is an exploded, partial perspective side view of the knot pusher instrument of FIG. 1;

FIG. 3 is a side view of the knot pusher instrument of FIG. 1, in partial section, showing a suture receiving tip translating from an operatively closed position to an operatively open position;

FIG. 4 is a cross-sectional view of the knot pusher instrument shown in FIG. 3, taken along line 4—4 of FIG. 3;

DETAILED DESCRIPTION OF THE INVENTION

Figure 5:
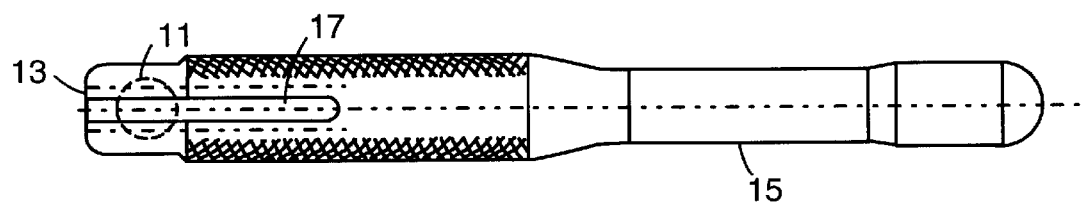
FIG. 5 is a top view of the handle of the knot pusher instrument according to the present invention.
Figure 6:
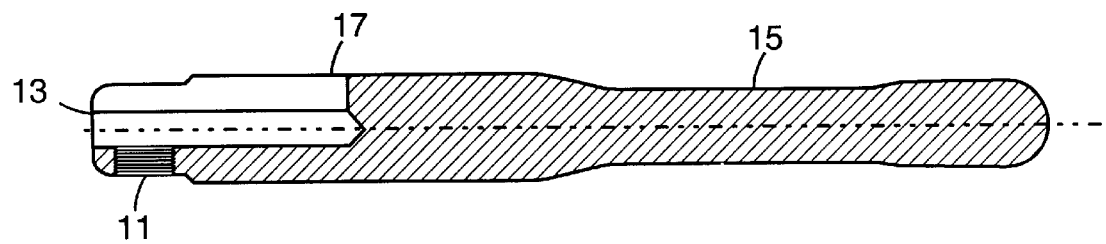
FIG. 6 is a cross-sectional side view of the knot pusher instrument shown in FIG. 5.
Figure 7:
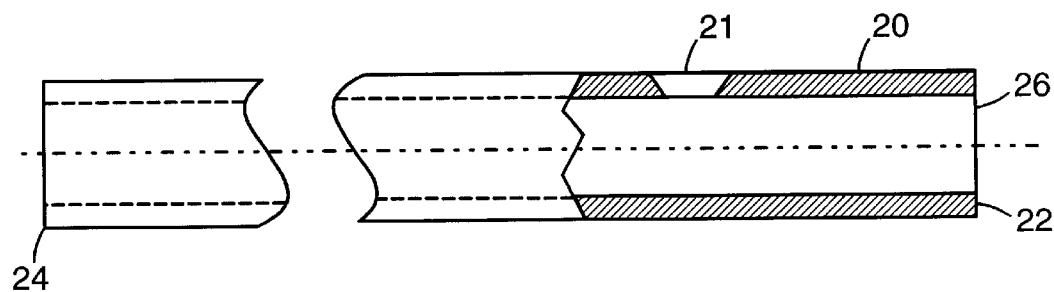
FIG. 7 is a partial cross-sectional view of the housing of the knot pusher instrument shown in FIGS. 1 and 3.

The present invention is more particularly described in the following examples that are intended as illustrative only since numerous modifications and variations therein will be apparent to those skilled in the art. As used in the specification and in the claims, "a" can mean one or more, depending upon the context in which it is used.

The present invention provides for a surgical knot pusher suitable for use in endoscopic surgery and other minimally invasive surgical techniques.

Referring to FIGS. 1–4, a medical knot typing instrument 10 according to the present invention generally comprises a tubular, elongated housing 20, a drive rod 60, a gripping mechanism 68, and a pushing mechanism 88. The housing 20 has a proximal end 22, a distal end 24, a passage 26 and a longitudinal axis A. The passage 26 of the housing 20 preferably has a circular cross section with a diameter D and defines a rod axis R therethrough that extends co-axial to the longitudinal axis A. The proximal end 22 of the housing 20 is attached to a handle 15 in fixed relation. The gripping mechanism 68 provides for releasably receiving and grasping a first length of a suture material proximate the distal end 24 of the housing 20. The pushing mechanism 88 provides for slidably pushing a knot formed from the first length of the suture material and an opposed second length of the suture material to a surgical site remote from the opening to the site.

Referring now to FIG. 1, a preferred embodiment of the knot tying instrument 10 according to the present invention is shown. The handle 15 is connected to the proximal end 22 of the housing 20 and is centered on the longitudinal axis A of the housing 20 so as to provide facility in using the instrument 10, regardless of the rotational position thereof about the longitudinal axis. The housing 20 may be connected to the handle 15 by any means known to one skilled is the art, such as by welding, chemical adhesive, and/or mechanical means. Two examples of a typical mechanical means are shown in FIGS. 1 and 3. In FIG. 1, the proximal end 22 of the housing 20 has a treaded surface that is screwed into a complementarily threaded center bore 13 extending longitudinally within the handle 15 for securing the housing 20 in relation to the handle 15. Alternatively, as shown in FIGS. 3, 4, 6 and 7, the housing 20 may have a housing bore 21 extending perpendicular to the longitudinal axis therethrough the side wall of the housing 20 into the passage 26 of the housing 20, and the handle 15 may have a handle bore 11 extending therethrough the side wall and into the center bore 13 of the handle 15. The housing 20 is inserted within the center bore of the handle 15 so that the housing bore is oriented co-axially with the handle bore of the handle 15, whereupon a fitting 19, such as a Luer lock, is removably inserted therein the housing bore and the handle bore to affix the handle 15 in relation to the housing 20.

Referring to FIGS. 1–3, 8A and 8B, the gripping mechanism 68 comprises a drive rod 60 and a suture receiving tip 40. The drive rod 60 has a front end 62, a rear end 64, and a longitudinal axis B that is co-axial to the rod axis R of the passage 26 of the housing 20. The drive rod 60 is slidably disposed within the passage 26 of the housing 20. The suture receiving tip 40 has a first end 44 and a second end 46. The second end 46 of the tip 40 is connected to the front end 62 of the drive rod 60 and defines a J-shaped hook 48 structure for receiving and capturing the first length of the suture. It is recognized that the suture receiving tip may be an integral member of the drive rod 60 without departing from the principles of the invention. It is preferred that the cross sectional width of the hook 48 between the first and second ends 44, 46 be less than the cross-sectional diameter D of the passage 26 of the housing 20 so that the first and second ends of the tip 40 may be received within the passage 26 of the housing 20. The first end 44 and the second end 46 of the tip 40 defines an gap 41 between the first and second ends 44, 46 of the tip 40 for receipt of the first length of the suture material within the U-shaped portion of the J-shaped hook 48 of the tip 40. Preferably, as shown in FIGS. 1–3 and 8A, the tip 40 is connected to the drive rod 60 and then bends outwardly relative to the longitudinal axis B of the drive rod 60 so that the tip 40 forms an acute angle γ relative to the longitudinal axis B of the drive rod 60. Thus, as will be appreciated by one skilled in the art, the tip 40 also forms the same acute angle γ relative to the rod axis R of the housing 20 thereby orienting the tip 40 in an angular plane relative to the rod axis R which allows for ease in viewing the tip 40 as the knot is formed and thence pushed into the surgical site. The acute angle γ of the tip 40 may range from 0 to 90 degrees, however, it is preferred that the acute angle γ of the tip 40 be approximately 45 degrees.

Referring to FIGS. 1–3 and 9, the rear end 64 of the drive rod 60 extends beyond the proximal end 22 of the housing 20, terminating in an operating mechanism. Preferably, the handle 15 provides a slot 17 wherein the operating mechanism extends outside the exterior surface of the handle 15, although it is to be recognized that the operating mechanism may be recessed within the handle 15 without departing from the principles of the invention.

The operating mechanism comprises a push button 75 connected to the rear end 64 of the drive rod 60 for selectively moving the drive rod 60 forward relative to the housing 20, which, as previously described, is fixed in relation to the handle 15. Moving the drive rod 60 forward opens the gap 41 between the first end 44 and second end 46 of the tip 40 as the front end 44 of the tip 40 is disposed a predetermined distance from the distal end 24 of the housing 20 as the drive rod 60 translates axially. The operating mechanism further comprises a spring 70 which applies rearwardly-directed force on the drive member. Thus, when the push button 75 is released, the spring 70 moves the drive rod 60 to a rearward position so as to bias the rod 60, and the connected tip 40, axially relative to the housing 20. Biasing the drive rod 60 rearwardly causes the first end 44 and the second end 46 of the tip 40 to be disposed within the passage 26 of the housing 20, which thereby forms an eyelet 43 having an aperture 45 for releasably capturing the first length of the suture as the gap 41 is operatively closed.

Figure 8A:
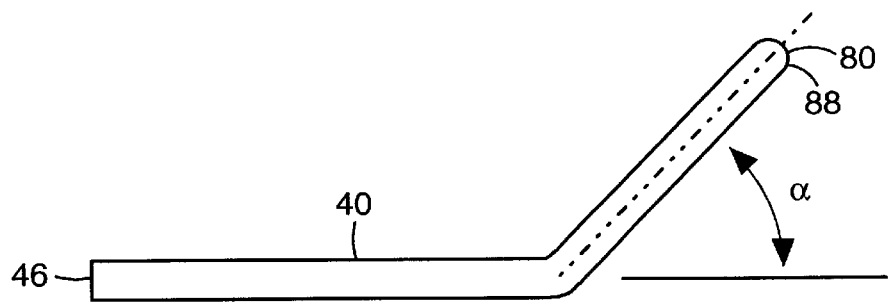
FIG. 8A is a side view of the suture retaining tip of the knot pusher instrument of the present invention.
Figure 8B:
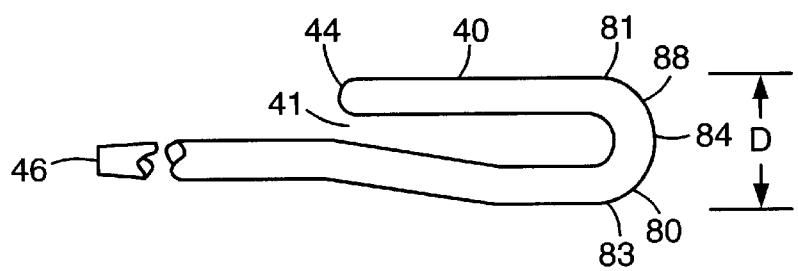
FIG. 8B is a top view of the suture retaining tip of the knot pusher instrument.
Figure 9:
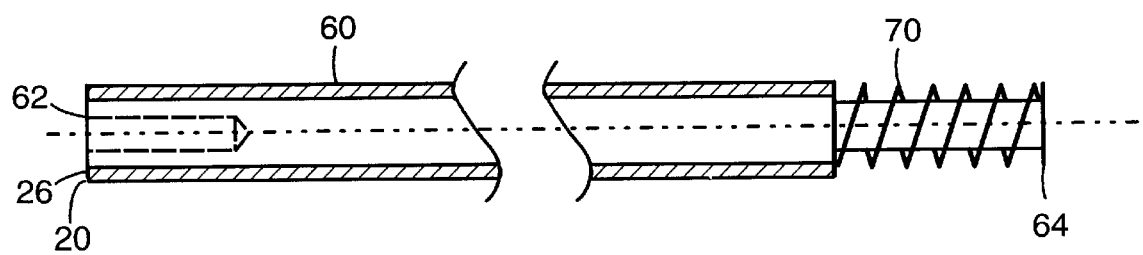
FIG. 9 is a side view of the drive rod, the spring, and the housing of the knot pusher instrument of the present invention, in partial section.

Referring to FIGS. 8A and 8B, the pushing mechanism 88 comprises a knot pushing surface 80 defining an arc 82 having a first curve end 81 and a second curve end 83. The arc 82 has a convex curvature with an apex 84 intermediate the first curve end 81 and the second curve end 83. The knot pushing surface 80 is formed from the exterior surface 42 of the tip 40 intermediate the first end 44 and second end 46 of the tip 40. It is preferred that the tip 40 have a circular cross section so that the exterior surface 42 of the tip 40 presents a smooth continuous surface which allows the surgical knot to slide freely without binding on the knot pushing surface 80.

Preferably, as shown in FIGS. 1, 3, 5 and 6, the handle 15 is contoured so that the handle 15 cross section tapers from a first handle cross sectional area to a second handle cross sectional area as the handle 15 extends from the proximal end 22 of the housing 20. The second handle cross sectional area is preferably smaller than the first handle cross sectional area so as to permit the user to cradle the handle 15 of the instrument 10 with the thumb and forefinger of one hand while operating the gripping mechanism 68 by selectively pushing and releasing the push button 75 using the forefinger of the same hand.

Referring now to FIG. 3, the user pushes or releases the push button 75 selectively to open or close the gap 41 of the tip 40. When the gap 41 is open, i.e., when the front end 42 of the tip 40 extends beyond the distal end 22 of the housing 20, a first length of a suture may be received therein the hook 48 of the tip 40 so that, when the gap 41 is closed upon the release of the push button 75, the length of suture may captured within the aperture 45 of the eyelet 43 formed when the first and second ends 44, 46 of the tip 40 are disposed within the passage proximate the distal end 24 of the housing 20 due to the rearward force applied by the spring 70.

Figure 10:
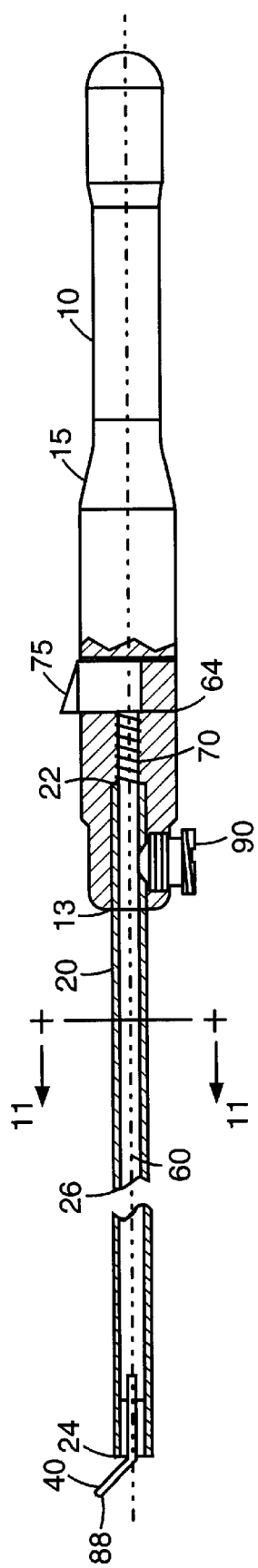
FIG. 10 is a side view of the knot pusher instrument of the present invention showing a flush port in communication with the housing, in partial section.
Figure 11:
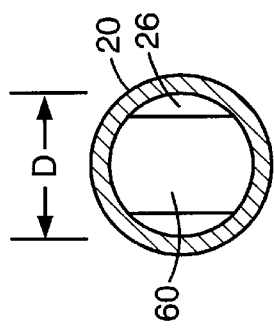
FIG. 11 is a cross-sectional view of the housing and the drive rod of the knot usher instrument shown in FIG. 11, taken along lines 11—11 of FIG. 10.

As shown in FIGS. 10 and 11, for structural purposes, and to ensure that the passage 26 of the housing 20 may be flushed clean upon application of cleaning fluid to a flush port 90 in fluid communication with the interior of the passage 26, it is preferred that the passage 26 have a circular cross section and that the drive rod 60 have a cross section in which two opposing side are complementarity shaped to match the interior surface of the passage 26 and in which the remaining two opposing sides have flat surfaces which form an opposing pair of debris passages 90 between the interior wall of the passage 26 of the housing 20 and the preferred flat surfaces of the drive rod 60. The debris passages 90 allow for the removal of debris within the passage 26 of the housing 20 upon the introduction of cleaning fluid into the flush port 90. The flushed debris pass out of the distal end 24 of the housing 20. It is to be recognized that other cross sectional shapes could be employed for the passage 26 and the drive rod 60 without departing from the principles of the invention.

The housing 20, drive rod 60, tip 40, and handle 15 may be made of any structurally adequate material which can be medically approved such as plastics, metal, composites, ceramics, and the like, as are well known in the art. Preferably the knot pushing surface 80 of the tip 40, or the tip 40 itself, is made of plastic or other materials compatible with the fragile hemocompatible coatings that are used on mechanical heart valves.

The method of tying a surgical knot using the preferred knot pusher instrument 10 of the present invention requires the suture material be inserted though the injured tissue at a surgical site remote from an opening in the patient's body. The suture material thus forms a first length of suture material having a first end and a second length of suture material having a second end. The two lengths of suture material are then delivered to a manipulation location from which the surgeon has access to the remote surgical site.

The surgeon then pushes the push button 75 to axially move the drive rod 60 relative to the distal end 24 of the housing 20. This axial movement of the drive rod 60 disposes the front end of the tip 40 a distance from the distal end 24 of the housing 20 and thereby causes the gap 41 of the tip 40 to become operatively open. The surgeon then hooks the first length of suture material using the J-shaped hook 48 formed between the drive rod 60 and the tip 40 so that the first length of the suture material may be received therein the operatively open gap 41 of the tip 40. The surgeon then releases the push button 75, which causes the drive rod 60, and the connected tip 40, to retract axially due to the rearward force applied by the spring 70. This causes the first length of the suture to be captured within the aperture 45 of the eyelet 43 formed when the first and second ends 44, 46 of the tip 40 are disposed within the distal end 24 of the housing 20 which operatively closes the annular gap 41 of the tip 40.

The second end of the suture material is "thrown" around the first length of suture adjacent the knot pushing surface 80 of the tip 40 which passes through the eyelet 43. If a surgeons' knot is desired, two wraps of the second end are thrown around the first length of suture. This forms a surgical throw of a type in which the second end may be tightened about the first suture length and moved along the first suture length. The first length of suture is then fed through the aperture 45 of the tip 40 until the knot pushing surface 80 is advanced up to and in engagement with the knot. A gentle, even pressure is exerted on the first and second ends of the suture to keep the first and second lengths of suture under tension as the knot pusher instrument 10 is advanced until the knot has been pushed all the way against the tissue being sutured at the surgical site.

If additional knot wraps are desired, the tip 40 of the knot pusher is withdrawn along the first length of suture material with the first length of suture remaining captured within the aperture 45 of the eyelet 43 of the tip 40 and a second throw of the second end of the suture is made around the first length of suture. Typically, a single wrap is thrown in the opposite sense from the previous throw so that a square knot or reef knot is formed. This second throw of the knot is advanced in the same way as the first throw until it is against the first throw of the of the knot. A series of square knots can be added to lock the suture in place by repeating the previously described procedure, alternating the direction of the knot thrown each time.

This throw-and-push, throw-and-push procedure very closely mimics the standard bimanual technique that is used for forming surgical knots in sutures, the only difference being that the knot is pushed forward by the knot pushing surface 80 of the instrument 10 instead of the surgeon's fingertip. Thus, the technique is very easy for the surgeon to learn and it can be done almost as rapidly as the standard bimanual knot tying technique. It should be noted that wasted effort, and more particularly, wasted time is minimized because the first length of the suture does not have to be recaptured and the second length of the suture does not have to be "inserted" into a knot surface groove or rethreaded each time a new throw is added to the knot being tied. This is especially important in the procedure of mitral valve replacement surgery because of the numerous sutures each requiring multiple knot throws.

Although the present invention has been described with reference to specific details of certain embodiments thereof, it is not intended that such detail should be regarded as limitations upon the scope of the invention except as and to the extent that they are included in the accompanying claims.

What is claimed is:

1. A medical instrument for positioning a suture knot formed from a first length of a suture and a second length of the suture at a surgical site remote from an opening to the site, the instrument comprising:

a tubular, elongated housing having a proximal end, a distal end and a passage defining a rod axis therethrough;

gripping mechanism for releasably grasping the first length of suture proximate said distal end of said tubular housing, said gripping mechanism including a drive rod slidably disposed within the passage of said housing and extending substantially co-axial to said rod axis; and a suture receiving tip having a generally hook shape with a first end and a second end; and including pushing mechanism movable with respect to said housing for slidably pushing a knot formed from the two lengths of suture member, and wherein said suture receiving tip forms an acute angle relative to the rod axis so that the hook of said suturing tip lies in a plane angled relative to the rod axis of said housing.

2. The medical instrument of claim 1, wherein said gripping mechanism comprises:

said drive rod having a front end and a rear end, slidably disposed within the passage of said housing and extending substantially co-axial to said rod axis; and said suture receiving tip having a first end and a second end, said tip forming a J-shaped hook, the second end of said tip connected to the front end of said rod, said rod slidably disposed within said housing from a drive rod retracted position, wherein the first end and the second end of said tip are disposed within the distal end of said housing thereby forming an eyelet having an aperture for releasably capturing the first length of the suture, to a rod extended position, wherein the first end of said tip is disposed a predetermined distance proximally from the distal end of said housing so that the first length of suture may be received within the hook of said tip.

3. The medical instrument of claim 2, wherein said tip has an exterior surface and wherein said pushing mechanism comprises:
   a knot pushing surface defining an arc having a convex curvature, said arc having a first curve end and a second curve end and an apex intermediate the first curve end and the second curve end of the arcs, wherein said knot pushing surface is formed from the exterior surface of said tip intermediate the first end and the second end of said tip.

4. The medical instrument of claim 3, wherein the hook of said tip has a circular cross-section.

5. The medical instrument of claim 1, wherein said acute angle is between 0 and 85 degrees.

6. The medical instrument of claim 1, wherein said acute angle is approximately 45 degrees.

7. The medical instrument of claim 2, further comprising an operating mechanism disposed at said rear end of said rod for operating said gripping mechanism.

8. The medical instrument of claim 7, wherein said operating mechanism comprises biasing mechanism for applying rearwardly-directed force on said rod to bias said rod axially relative to said housing.

9. The medical instrument of claim 8, wherein said biasing mechanism comprises a spring.

10. The medical instrument of claim 8, wherein said operating mechanism further comprises an actuating mechanism for applying frontally-directed force on said rod member to overcome said rearwardly-directed force thereon.

11. The medical instrument of claim 10, wherein said actuating mechanism comprises a push button attached to the rear end of said rod.

12. The medical instrument of claim 1, further comprising a handle attached adjacent the proximal end of said housing, wherein said housing has a longitudinal axis, and wherein said handle extends longitudinally from said housing so that the longitudinal axis of the handle and the rod axis of the housing are co-axial.

13. A medical instrument for positioning a suture knot formed from a first length of a suture and a second length of the suture at a surgical site remote from an opening to the site, the instrument comprising:
   a tubular, elongated housing having a proximal end, a distal end and a passage defining a rod axis therethrough, the passage having a first cross-section;
   a suture receiving tip having an exterior surface, a first end and a second end, said tip forming a J-shaped hook having a cross-section substantially equal to the first cross-section and defining a gap formed between the first end and the second end of said tip;
   a drive rod slidably disposed within the passage of said housing and extending substantially co-axial to said rod axis, said drive rod having a front end and a rear end, wherein the front end of said drive rod is connected to the second end of said tip so that said tip is selectively operable between a open and a closed position; and
   a knot pushing surface formed from the exterior surface of said tip intermediate the first end and the second end of said tip,
wherein, in the closed position of the tip, axial movement of said drive rod relative to said housing causes the first end and the second end of said tip to be received within the passage of said housing proximate the distal end of said housing so that an eyelet having an aperture for releasably capturing the first length of the suture is formed, and wherein, in the open position of the tip, axial movement of said drive rod relative to said housing causes the first end of said tip to extend beyond the distal end of said housing so that the length suture may be inserted therein the gap of the hook of said tip, and wherein said tip forms an acute angle relative to the rod axis so that the hook of said suturing receiving tip lies in a plane angled relative to the rod axis of said housing.

14. The medical instrument of claim 13, wherein said knot pushing surface comprises a knot pushing surface defining an arc having a convex curvature, said arc having a first curve end and a second curve end and an apex intermediate the first curve end and the second curve end of the arcs.

15. The medical instrument of claim 14, wherein said tip has a circular cross-section.

16. The medical instrument of claim 13, wherein said acute angle is approximately 45 degrees.

17. The medical instrument of claim 13 further comprising a spring disposed at the rear end of said rod for applying rearward-directed force on said rod to bias said rod axially relative to said housing.

18. The medical instrument of claim 17, further comprising a push button connected proximate the rear end of said rod for applying frontally-directed force on said rod member to overcome said rearwardly-directed force thereon by said spring.

19. The medical instrument of claim 13 further comprising a handle attached adjacent the proximal end of said housing, said housing having a longitudinal axis, and said handle extending laterally from the longitudinal axis of said housing.

20. The medical instrument of claim 19, wherein the handle is contoured for grasping by a surgeon's hand.

21. A method of tying a length of surgical suture material at a surgical site remote from an opening to the site using a surgical knot instrument comprising a tubular housing having a distal end and a passage defining a rod axis therethrough, a suture receiving tip forming a J-shaped hook having a first end, a second end, and an exterior surface, a drive rod having a front end connected to the second end of said suture receiving tip, said drive rod slidably disposed within the passage of the tubular housing, and a knot pushing surface formed from the exterior surface of said tip, where the suture material has been inserted through injured tissue at the site and two lengths of the suture material, having a first length and a second length respectively, extend to a manipulation area remote from the surgical site, comprising the steps of:
   a) extending said drive rod relative to the distal end of said housing so that the front end of said tip is disposed a distance from said housing and feeding the first suture length therein the hook of said tip;
   b) retracting said drive rod relative to the distal end of said housing to capture the first suture length within an aperture of an eyelet formed when the first end and the second end of said tip are disposed within the passage of said housing;

c) tying, at the manipulation area, in the suture material adjacent the knot pushing surface, a surgical throw of a type in which the second length of the suture may be tightened about the first suture length and moved along the first suture length;

d) feeding the first suture length through the aperture of said tip to move said knot tier forward along the first suture length until said knot pushing surface is brought into engagement with the surgical knot;

e) pushing the knot pushing surface with the surgical knot engaged to the surgical site while applying tension to the first end of the first suture length and the second end of the second suture length; and f) repeating steps c-e until a secure knot is formed.

22. A method of tying surgical sutures and positioning a suture knot formed from a first length of a suture and a second length of the suture at a surgical site remote from an opening to the site, comprising:

a) providing a surgical knot instrument, comprising:

a tubular, elongated housing having a proximal end, a distal end and a passage defining a rod axis therethrough, the passage having a first cross-section;

a suture receiving tip having an exterior surface, a first end and a second end, said tip forming a J-shaped hook having a cross-section substantially equal to the first cross-section and defining an annular gap formed between the first end and the second end of said tip;

a drive rod slidably disposed within the passage of said housing and extending substantially co-axial to said rod axis, said drive rod having a front end and a rear end, wherein the front end of said drive rod is connected to the second end of said tip so that said tip is selectively operable between a open and a closed position; and a knot pushing surface formed from the exterior surface of said tip intermediate the first end and the second end of said tip, wherein, in the closed position of the tip, axial movement of said drive rod relative to said housing causes the first end and the second end of said tip to be received within the passage of said housing proximate the distal end of said housing so that an eyelet having an aperture for releasably capturing the first length of the suture is formed, and wherein, in the open position of the tip, axial movement of said drive rod relative to said housing causes the first end of said tip to extend beyond the distal end of said housing so that the length suture may be inserted therein the gap of the hook of said tip;

b) extending said drive rod relative to said housing so that the gap of said tip is opened and feeding the first suture length within the hook of said tip;

c) retracting said drive rod relative to said housing to capture the first suture length within the aperture of the eyelet of said tip formed when portions of the hook of said tip are disposed within the passage of said housing;

d) tying, in the suture material adjacent the knot pushing surface, a surgical throw of a type in which the second end may be tightened about the first suture length and moved along the first suture length;

e) feeding the first suture length through the aperture of said tip to move said knot tier forward along the first suture length until said knot pushing surface is brought into engagement with the surgical knot;

f) pushing the knot pushing surface with the surgical knot engaged to the surgical site while applying tension to the first end of the first suture length and the second end of the second suture length; and g) repeating steps d-f until a secure knot is formed.

* * * * *

UNITED STATES PATENT AND TRADEMARK OFFICE
CERTIFICATE OF CORRECTION

PATENT NO.    : 6,258,106 B1
DATED         : July 10, 2001
INVENTOR(S)   : Robert F. Leonard It is certified that error appears in the above-identified patent and that said Letters Patent is hereby corrected as shown below:

Column 1,
Line 59, replace "patent material" with -- patent atrial --;

Column 6,
Line 65, replace "knot typing" with -- knot tying --;

Column 7,
Line 60, replace "an gap" with -- a gap --.

Signed and Sealed this

Fifth Day of March, 2002

*Attest:*

*Attesting Officer*

JAMES E. ROGAN
*Director of the United States Patent and Trademark Office*